United States Patent
Pryor

(10) Patent No.: US 6,904,806 B2
(45) Date of Patent: Jun. 14, 2005

(54) ELECTRONIC INTELLIGENT INDENTER

(75) Inventor: Roger W. Pryor, Bloomfield Hills, MI (US)

(73) Assignee: Wayne State University, Detroit, MI (US)

(*) Notice: Subject to any disclaimer, the term of this patent is extended or adjusted under 35 U.S.C. 154(b) by 413 days.

(21) Appl. No.: 10/197,142

(22) Filed: Jul. 18, 2002

(65) Prior Publication Data

US 2004/0011118 A1 Jan. 22, 2004

(51) Int. Cl.[7] .................................................. G01H 5/00
(52) U.S. Cl. ....................................................... 73/597
(58) Field of Search .............................. 73/150 R, 597, 73/81, 82, 83; 356/630; 181/123, 124

(56) References Cited

U.S. PATENT DOCUMENTS

| | | |
|---|---|---|
| 2,663,185 A | 12/1953 | Broschke |
| 3,653,256 A | 4/1972 | Mashimo |
| 3,805,598 A | 4/1974 | Corcoran |
| 4,059,990 A | 11/1977 | Glover et al. |
| 4,551,030 A * | 11/1985 | Luukkala et al. ............... 374/5 |
| 4,820,051 A | 4/1989 | Yanagisawa et al. |
| 5,038,615 A * | 8/1991 | Trulson et al. ................. 73/597 |
| 5,146,779 A | 9/1992 | Sugimoto et al. |
| 5,438,872 A | 8/1995 | Kobayashi et al. |
| 5,553,486 A | 9/1996 | Bonin |
| 6,142,010 A | 11/2000 | Merck, Jr. et al. |
| 6,247,355 B1 | 6/2001 | Suresh et al. |
| 6,343,502 B1 | 2/2002 | Subhash et al. |
| 6,349,595 B1 | 2/2002 | Civolani et al. |

* cited by examiner

Primary Examiner—Robert Raevis
(74) Attorney, Agent, or Firm—John A. Miller; Warn, Hoffmann, Miller & LaLone, P.C.

(57) ABSTRACT

An electronic intelligent indenter system that determines the hardness and the case depth of a hardened portion of a test part in a non-destructive manner. The system employs an electronic indenter tool having a tip. To determine the depth of the case hardened portion of the part, the indenter tip is placed in contact with the surface of the part, and a laser emits a laser beam pulse that impinges the surface of the part proximate the tip. The laser beam generates ultrasonic waves that propagate into the part. The ultrasonic waves reflect off of a transition between the case hardened portion and an unhardened portion of the part. A detector in the indenter system detects the reflected ultrasonic waves. The ultrasonic waves cause the detector to generate a signal identifying the time between when the laser pulse is emitted and when the reflected wave is received. The signal is analyzed by a controller that compares the signal to a standard of calibration for a reflected wave from a hardened portion of a calibration part having a greater depth than the test part.

20 Claims, 1 Drawing Sheet

ELECTRONIC INTELLIGENT INDENTER

BACKGROUND OF THE INVENTION

1. Field of the Invention

This invention relates generally to an electronic indenter system that measures the hardness and depth of a hardened portion of a part and, more particularly, to an electronic intelligent indenter system that measures the hardness and depth (case depth) of a hardened portion of a part in a non-destructive manner, where the system includes an electronic indenter tool, a laser for producing ultrasonic waves in the part, and an integral detector for detecting ultrasonic waves reflected from the transition boundary between the hardened portion and the unhardened portion of the part.

2. Discussion of the Related Art

The wear surface of certain machine parts, such as crankshafts, axles, gears, piston rods, shafts, bearing sleeves, ball bearings, tapered bearings, etc., is sometimes case hardened so that the part has a longer life and does not readily fail. Hardness is an intrinsic property of a material that is a result of the fundamental crystalline structure of the material. The CRC Handbook of Chemistry and Physics defines hardness as a property of substances determined by their ability to abrade or indent one another. Case hardening is typically provided by thermally treating the wear surface of the part, or providing some form of atomic displacement (stress), to add strength to the surface of the part. Typical hardened depths of a part are on the order of 0.5 mm–1 mm.

In order to ensure that a part is properly hardened, indenter hardness measurement systems are employed to test the part to determine the hardness and case depth of the hardened portion. International standards have been established for the precise procedures and equipment to be used in performing such hardness tests. A typical hardness measurement system that measures the hardness of a surface of a part employs an indenter tool having a tip that indents or pits the surface of the part under a known load. The tip of the indenter tool can have any one of several shapes, including spherical, diamond, pyramidal, etc. Either the displacement of the tool or the size of the formed pit in the surface of the part is then measured, depending upon the standard system used, to determine the hardness of that hardened portion.

Known hardness measurement systems that determine the depth of the case hardened portion employ processes that are typically destructive to the part. Further, the processes are costly and time consuming. Particularly, known indenter hardness measurement systems that determine the depth of the hardened portion of a part require that the part be sectioned and the sectioned surface be polished to measure the case hardness across the sectioned surface at predetermined intervals to identify the transition between the case hardened portion and the unhardened portion, and thus the depth of the case hardened portion. If the part includes multiple case hardened areas, the difficulty and expense of the measurement task increases proportionately.

In one known hardness test, referred to as a Brinell test, a load in the range of 500–3000 kg is applied to an indenter tool having a 10 mm steel or tungsten ball tip. The indentation pit made by the indenter tool is measured with a microscope calibrated in millimeters. The hardness is then calculated as:

$$H_B = \frac{L}{\pi D * \frac{(D - \sqrt{D^2 - d^2})}{2}} \quad (1)$$

In equation (1), L is the value of the load, D is the diameter of the ball tip, and d is the diameter of the indentation pit.

In another known hardness test, referred to as the Rockwell or Rockwell superficial test, the hardness of the part is determined by measuring the difference in penetration depth of the tool into the part between a light (minor) first load and a heavier (major) second load with either a spherically terminated conical diamond tip or a steel ball tip indenter tool. In other words, the microscopic distance that the indenter tool moves into the part under the first and second loads is measured to determine the hardness. In the Rockwell test, the minor load is typically about 10 kg and the major load is 60–150 kg. The Rockwell test can employ an electronic Instron Machine, model 2000 to perform the hardness analysis. This is the primary method of hardness testing under consideration in this disclosure.

In another test, referred to as the Vickers test, the indenter tip is pyramidal in shape, rather than spherical, and the loads range from 1–120 kg. The hardness number is calculated as the ratio of the load applied to the surface of the indentation by:

$$H_v = \frac{1.8544P}{D^2} \quad (2)$$

In equation (2), P is the load pressure applied and D is the diagonal of the indentation.

SUMMARY OF THE INVENTION

In accordance with the teachings of the present invention, an electronic intelligent indenter system is disclosed that is capable of measuring the hardness and the depth of a case hardened portion of a test part in a non-destructive manner, i.e., without having to section the part. The system employs an electronic indenter tool having an indenter tip, such as a spherically terminated conical diamond tip. To measure the hardness, a known load is applied to the tool to indent the surface of the hardened portion of the part. The system measures the movement of the tip as it indents the surface of the part, or measures the size of the pit caused by the tip to determine the hardness.

To measure the depth of the case hardened portion of the part, the indenter tip is placed in contact with the hardened surface of the part. A laser emits a laser beam pulse that impinges the surface of the part proximate the tip. The laser beam pulse generates ultrasonic waves that propagate into the part. A portion of the ultrasonic waves reflect from the transition surface formed between the case hardened portion and an unhardened portion of the part. An ultrasonic detector in the indenter system, such as a piezoelectric transducer, detects the reflected ultrasonic waves. The detector generates a signal indicative of the time that the reflected wave is received. The signal from the ultrasonic detector is analyzed by a controller that compares the received signal from the part under test to the received signal from a calibration standard sample having a greater case depth than that of the part under test.

Additional objects, advantages and features of the present invention will become apparent from the following description and appended claims, taken in conjunction with the accompanying drawings.

DETAILED DESCRIPTION OF THE EMBODIMENTS

Figure 1:
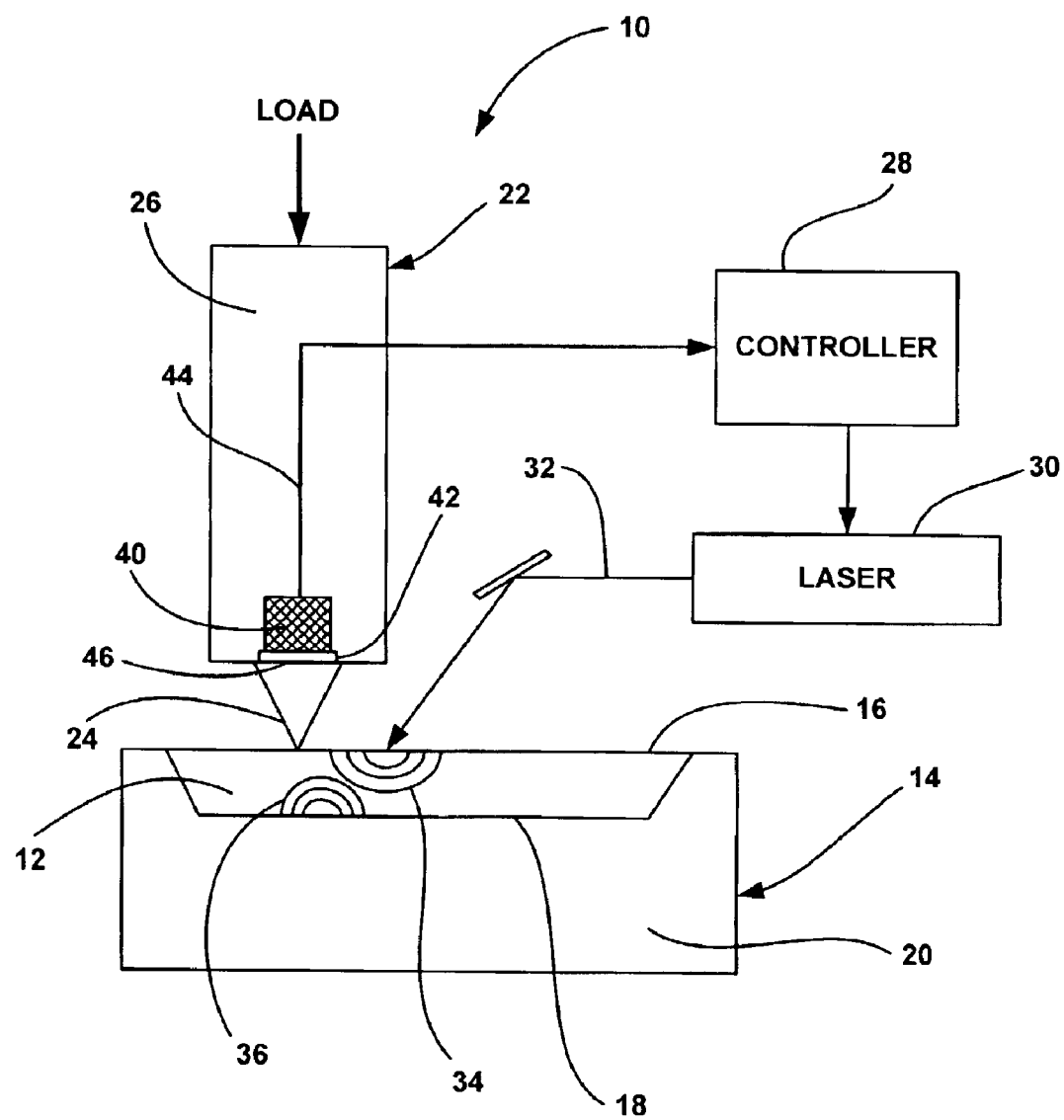
FIG. 1 is a plan view of an electronic intelligent indenter hardness measurement system, according to an embodiment of the present invention.

The following description of the embodiments of the invention directed to an electronic intelligent indenter hardness measurement system that measures the hardness and depth of a case hardened portion of a part is merely exemplary in nature, and is in no way intended to limit the invention or its applications or uses.

FIG. 1 is a plan view of an electronic intelligent indenter hardness measurement system 10 that measures the hardness and depth of a case hardened portion 12 of a part 14, according to an embodiment of the present invention. The part 14 can be any machine part that requires a case hardened surface to provide resistance against wear or the like. Any traditional technique can be employed to harden a surface 16 of the part 14 to provide the hardened portion 12 so that it extends a certain distance into the part 14. A transition 18 is defined between the case hardened portion 12 and an unhardened portion 20 of the part 14. The part 10 can be made of any material known in the industry that is capable of being hardened, usually steel.

The system 10 includes an electronic indenter tool 22 including a tip 24 positioned in contact with the surface 16 of the part 14, as shown. In one embodiment, the tip 24 is a diamond tip having any suitable end shape, such as a diamond, ball or pointed end. However, as will be appreciated by those skilled in the art, the tip 24 can be made of any material and have any shape suitable for the purposes described herein. The tip 24 is mounted to a body portion 26 of the tool 22 by any suitable technique known in the art. Any suitable hardness testing technique, such as the Brinell, Rockwell or Vickers hardness test discussed above, can be used to determine the hardness of the hardened portion 12. Particularly, a predetermined load is applied to the body portion 26 towards the part 14 so that the tip 24 moves into and indents the surface 16 of the part 14. Microscopic measurements of the movement of the tool 22 can be taken based on the load to give a measurement of the case hardness of the hardened portion 12. Alternately, the size of the indentation pit can be measured, as needed, based on the load to determine the hardness. The system 10 can employ the electronic Instron Machine, referred to above, for this purpose.

According to the invention, the system 10 also determines the case depth of the hardened portion 12 without the need to section the part 14 and make measurements of the hardness along the sectioned profile of the part 14, as was done in the prior art. Particularly, the system 10 employs a laser 30, such as an Nd:YAG laser, that emits a laser beam interrogation pulse 32 directed towards the surface 16 of the part 14 proximate the location where the tip 24 contacts the surface 16. Other lasers suitable for the purposes described herein can also be used. A controller 28 controls the operation of the laser 30 by activating the laser 30 for the desired period of time. In one embodiment, the pulse has a duration of 5 ns. However, this is by way of a non-limiting example in that other suitable pulse durations can be used within the scope of the present invention. The laser beam interrogation pulse 32 generates broadband ultrasonic waves 34 that propagate into the part 14. Ultrasonic is used herein to describe all sound energy signals, including sub-sonic signals.

When the ultrasonic waves 34 reach the transition 18 between the case hardened portion 12 and the unhardened portion 20 of the part 14, some of the ultrasonic waves 34 propagate through the transition 18 into the unhardened portion 20 and some of the ultrasonic waves 34 are reflected towards the surface 16 as reflected ultrasonic waves 36. When the reflected waves 36 reach the surface 16, they enter the tip 24 and propagate therethrough to be detected by a detector 40. The detector 40 is coupled to the tip 24 by any suitable technique so that the sound energy propagates to the detector 40 with minimal attenuation. In one embodiment, the detector 40 is a piezoelectric transducer (PZT). However, as will be appreciated by those skilled in the art, the detector 40 can be any detector suitable for the purposes described herein. The detector 40 may be bonded to a thin membrane 42 in the body 26 or directly to the top of the diamond indenter tip 46. The detector 40 generates electrical signals 44 indicative of the intensity of the reflected waves 36 that are sent to the controller 28.

The controller 28 can be any suitable computer-based device for the purposes described herein. The controller 28 identifies a time period from when the laser beam pulse 32 is emitted to when the reflected ultrasonic waves 36 are received by the detector 40 to give the depth of the transition 18. The controller 28 activates the laser 30 and knows when the detector 40 receives the reflected waves 36 by the intensity of the electrical signal from the detector 40. The controller 28 uses the velocity of sound waves in steel and diamond to determine the time of flight (TOF) of the ultrasonic waves 34 and 36. Particularly, the velocity of sound in diamond is:

$$V_{longitudinal} = 1.8 \times 10^4 \text{ m/sec}$$

$$V_{transverse} = 1.2 \times 10^4 \text{ m/sec}$$

And, the velocity of sound in steel is:

$$V_{longitudinal} = 5.854 \times 10^3 \text{ m/sec}$$

$$V_{transverse} = 3.150 \times 10^3 \text{ m/sec}$$

By knowing the velocity of sound in diamond and the velocity of sound in hardened steel, as given above, the depth of the case hardened portion 12 can be determined by measuring the TOF of the ultrasonic waves 34 and 36. The controller 28 compares the TOF of the ultrasonic waves to the TOF of an ultrasonic wave propagating through a hardened material that is much thicker than the hardened portion 12 to give a calibration standard, and thus an accurate measurement.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A system for determining the depth of a case hardened portion of a test part, said system comprising:

an electronic indenter tool, said indenter tool including a body portion and a tip mounted thereto, said tip being positioned in contact with an outer surface of the hardened portion, said indenter tool further including a detector mounted within the body portion;

a device for generating sound waves in the part, said sound waves being reflected off of a transition between the hardened portion and an unhardened portion of the part, said reflective waves propagating into the tip and being detected by the detector, said detector generating an electrical signal indicative of the intensity of the reflected sound waves received by the detector; and a controller, said controller being responsive to the electrical signal from the detector, said controller determining the depth of the hardened portion based on the time of flight the sound waves propagate in the test part.

2. The system according to claim 1 wherein the controller compares the time of flight of the sound waves to a calibration standard, said calibration standard including time of flight information of sound waves propagating through a calibration part having a hardened portion with a depth significantly deeper than the hardened portion of the test part.

3. The system according to claim 1 wherein the device is a laser, said laser generating a laser beam pulse directed towards the hardened portion proximate the tip of the tool, said laser beam pulse generating the sound waves in the test part.

4. The system according to claim 1 wherein the system also determines the hardness of the hardened portion of the test part.

5. The system according to claim 4 wherein the system determines the hardness of the hardened portion by applying a predetermined load to the indenter tool and measuring the distance that the tip of the tool moves into the test part.

6. The system according to claim 4 wherein the system determines the hardness of the hardened portion by applying a predetermined load to the indenter tool and measuring the size of an indentation in the test part caused by the tip of the tool.

7. The system according to claim 1 wherein the tip is a diamond tip.

8. The system according to claim 1 wherein the detector is a piezoelectric transducer.

9. The system according to claim 1 wherein the sound waves are ultrasonic waves.

10. An indenter system for determining the case depth of a hardened portion of a test part, said system comprising:

an electronic indenter tool, said indenter tool including a body portion and a tip mounted thereto, said tip being positioned in contact with an outer surface of the hardened portion, said indenter tool further including a piezoelectric transducer;

a laser, said laser directing a laser beam pulse to the outer surface of the hardened portion of the part proximate the tip, said laser beam pulse generating ultrasonic waves that propagate into the part, said ultrasonic waves being reflected off of a transition between the case hardened portion and an unhardened portion of the part, said reflective waves propagating into the tip and being detected by the transducer, said transducer generating an electrical signal indicative of the intensity of the reflected waves received by the transducer; and a controller, said controller activating the laser, said controller being responsive to the electrical signal from the transducer, said controller determining the depth of the case hardened portion based on time of flight of the ultrasonic waves through the test part, wherein the controller compares the time of flight of the ultrasonic waves to a calibration standard, said calibration standard including time of flight information of ultrasonic waves propagating through a calibration part having a hardened portion with a depth significantly deeper than the hardened portion of the test part.

11. The indenter system according to claim 10 wherein the system also determines the hardness of the hardened portion of the test part.

12. The indenter system according to claim 11 wherein the system determines the hardness of the hardened portion by applying a predetermined load to the indenter tool and measuring the distance that the tip of the tool moves into the test part.

13. The indenter system according to claim 11 wherein the system determines the hardness of the hardened portion by applying a predetermined load to the indenter tool and measuring the size of an indentation in the test part caused by the tip of the tool.

14. The indenter system according to claim 10 wherein the tip is a diamond tip.

15. A method of determining the case depth of a hardened portion of a test part, comprising:

positioning a tip of an electronic indenter tool in contact with an outer surface of the hardened portion, said indenter tool including a body portion and a detector;

directing a laser beam pulse at the surface of the hardened portion proximate the tip, said beam pulse generating sound waves in the part that propagate into the part and are reflected off of a transition between the case hardened portion and an unhardened portion of the part;

detecting the reflected sound waves by the detector;

generating an electrical signal in the detector indicative of the intensity of the sound waves detected by the detector; and determining the depth of the hardened portion based on the time from when the laser beam pulse is emitted to when the electrical signal is received.

16. The method according to claim 15 further comprising comparing the time to a calibration standard, said calibration standard including time of flight information of sound waves propagating through a calibration part having a hardened portion with a depth significantly deeper than the hardened portion of the test part.

17. The method according to claim 15 further comprising determining the hardness of the hardened portion of the test part.

18. The method according to claim 15 wherein the tip is a diamond tip.

19. The method according to claim 15 wherein the detector is a piezoelectric transducer.

20. The method according to claim 15 wherein the sound waves are ultrasonic waves.

* * * * *